(12) United States Patent
Annen et al.

(10) Patent No.: US 6,251,679 B1
(45) Date of Patent: Jun. 26, 2001

(54) METHOD FOR MEASURING POLLUTANT FORMATION

(75) Inventors: Kurt Annen, Rowely; David B. Stickler, Carlisle, both of MA (US)

(73) Assignee: Aerodyne Research, Inc., Billerica, MA (US)

( * ) Notice: Subject to any disclaimer, the term of this patent is extended or adjusted under 35 U.S.C. 154(b) by 0 days.

(21) Appl. No.: 09/179,037

(22) Filed: Oct. 26, 1998

(51) Int. Cl.⁷ .................................................... G01N 21/76
(52) U.S. Cl. .............................. 436/34; 436/116; 436/172
(58) Field of Search ................................ 436/34, 116, 117, 436/118, 172; 250/361 C

(56) References Cited

U.S. PATENT DOCUMENTS

| | | | |
|---|---|---|---|
| 3,973,914 | * | 8/1976 | VanHeusden . |
| 4,657,744 | * | 4/1987 | Howard ................................... 422/52 |
| 4,822,564 | * | 4/1989 | Howard ................................... 422/52 |
| 4,897,548 | * | 1/1990 | Dome et al. ...................... 250/361 C |
| 5,185,268 | * | 2/1993 | Bonometti et al. ................... 436/114 |
| 5,300,441 | * | 4/1994 | Fujinari et al. ....................... 436/110 |

OTHER PUBLICATIONS

A. Leipertz, R. Obertacke, F. Wintrich; *Industrial Combustion Control Using UV Emission Tomography*, 1996.

* cited by examiner

*Primary Examiner*—Jeffrey Snay
(74) *Attorney, Agent, or Firm*—Cesari & McKenna

(57) ABSTRACT

Diagnostic methods for determining an instantaneous rate of pollutant formation in a combustion system are based on measurement of chemiluminescence intensity generated simultaneously with the formation of the pollutant. The chemiluminescent signal is generated by an analog reaction which occurs in parallel with a key step in the formation of a specific pollutant of interest. The connection between the analog reaction and the pollution reaction is such that the chemiluminescent signal indicates the local, instantaneous formation rate of the pollutant of interest.

29 Claims, 1 Drawing Sheet

METHOD FOR MEASURING POLLUTANT FORMATION

This invention was made with government support under NASA SBIR contract no. NAS3-97079. The government has certain rights in this invention.

BACKGROUND OF THE INVENTION

Nitric oxide (NO) is a serious atmospheric pollutant readily formed when fuels are combusted with any oxidant containing oxygen and nitrogen. Minimization of NO production has become a key goal of current combustor development.

To date, such efforts have relied on measurements of the total quantity of NO exiting a combustor or on measurements of local NO concentrations within the combustion volume. The gross measurement has the advantage of being relatively simple but provides no direct data on the spatial distribution of NO formation in the combustor. On the other hand, sampling as a function of position reveals the spatial distribution of NO concentration but the available implementations—intrusive sampling probes or laser-based optical sampling—are less-than-ideal for combustor development work. Intrusive probes perturb flow through the combustion volume and are subject to problems related to premature degradation of the sample, and furthermore each probe provides data for only one location at a time. Laser-based optical sampling requires a sophisticated and complex optical system, as well as open optical access to the combustion volume.

Their other strengths and weaknesses aside, both the gross and local types of measurement show only the instant quantity of NO present, which is a result of the entire previous combustion history of the gas sample examined. Neither approach is capable of indicating the local rate of NO formation, a parameter critical to intelligent refinement of combustor design.

SUMMARY OF THE INVENTION

The present invention provides diagnostic methods for determining an instantaneous rate of pollutant formation due to a combustion reaction of reactants in a combustion system, based on measurement of chemiluminescence intensity generated simultaneously with the formation of the pollutant. The method of the invention measures the chemiluminescent signal due to an analog reaction which occurs in parallel with a key step in the formation of a specific pollutant of interest. The connection between the analog reaction and the pollution reaction is such that the chemiluminescent signal indicates the local, instantaneous formation rate of the pollutant of interest.

The analog reaction may involve species normally present under the conditions giving rise to the formation of the pollutant, as in the case of naturally occurring combustion radicals which react to emit light. For example in hydrocarbon flames, OH*, which undergoes chemiluminescent decay, is produced naturally, primarily in accordance with $$CH + O_2 \rightarrow CO + OH^* \quad \text{(equation 1)}.$$

Having similar reactants to the initiating reaction for generation of NO by the so-called "prompt" mechanism, $$CH + N_2 \rightarrow HCN + N,$$

makes equation 1 a possible analog reaction. Such a correlation would allow NO formation by this route to be monitored by observation of chemiluminescence from OH* occurring naturally in combustion systems. In other cases, the analog reaction is undergone by one or more species provided by an additive which is extraneous to the principal combustion process.

In a preferred embodiment, the technique includes introducing a boron-containing additive into the combustion system and identifies formation of nitric oxide based on light emitted by species provided by the additive. Under combustion conditions typically used for fossil fuels, notably in the presence of excess oxidant, the dominant mode of NO generation is the "thermal" mechanism reported by Zel'dovich:

$$N_2 + O \rightarrow NO + N \quad \text{(reaction 1)}$$
$$N + O_2 \rightarrow NO + O.$$

The first reaction, which typically controls the overall process, is controlled by the concentration of oxygen radicals and the local gas temperature. The boron-containing additive enables formation of BO radical, which makes possible the analog reaction. The parallel reaction to reaction 1, also governed by oxygen radical concentration and temperature, forms excited $BO_2^*$ in the reaction volume:

$$BO + O + M \rightarrow BO_2^* + M.$$

The transition of the excited $BO_2^*$ to the ground state, $$BO_2^* \rightarrow BO_2 + h\nu,$$

follows essentially immediately from the parallel reaction, resulting in the familiar "green" chemiluminescent emission, for which the main emission bands are at 518, 548 and 580 nm. The invention exploits the strong correlation between the rate-controlling step of the thermal NO mechanism and the coupled parallel reaction and chemiluminescent step comprising the analog reaction in order to directly determine the NO formation rate from $BO_2^*$ chemiluminescence intensity.

Boron compounds appropriate as additives for this embodiment include diborane ($B_2H_6$) and trialkyl borates such as trimethyl borate ($B(OCH_3)_3$) and triethyl borate ($B(OC_2H_5)_3$). Diborane has a high vapor pressure and is attractive as a seed compound for introduction into gaseous fuels or with air or some other gaseous oxidant. Trimethyl borate is a liquid and is especially attractive for adding to liquid fuels. In general, it is desirable for such an additive to have a vaporization temperature similar to the vaporization temperature of the fuel with which it is mixed.

As used herein, the phrase "due to a combustion reaction of reactants" as applied to pollutant generation encompasses formation during or as a byproduct of the combustion reaction or an ensuing post-combustion reaction. The phrase "reaction volume" refers to the space in which the reaction generating the pollutant occurs, whether it is the combustion volume or a post-combustion volume. Also, an additive's "providing a species" for generating a chemiluminescent signal is intended to encompass cases in which the additive itself is the species and cases in which the additive somehow reacts or decomposes so as to generate the species. An "analog reaction" denotes a reaction that occurs in parallel with the reaction giving rise to the pollutant, or a series of reactions including one such step. The analog reaction may further encompass additional steps, for example, decay with photon emission, of an excited species created during the parallel reaction.

BRIEF DESCRIPTION OF THE DRAWINGS

The invention description below refers to the accompanying drawings, of which.

DETAILED DESCRIPTION OF THE INVENTION

Figure 1:
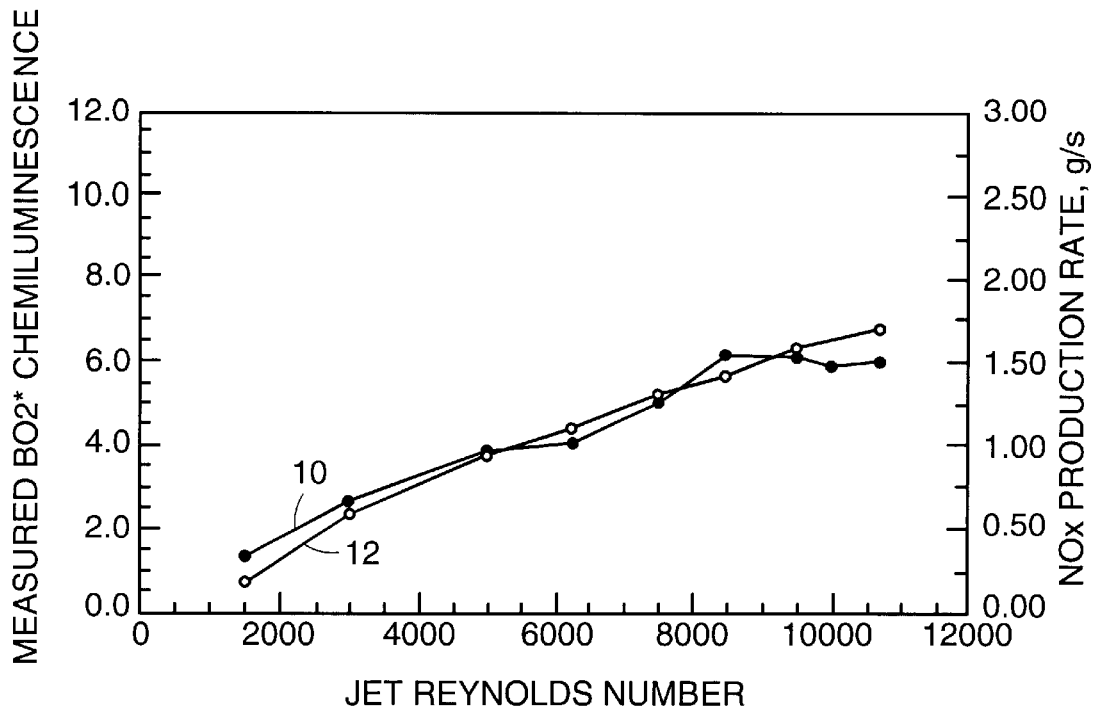
FIG. 1 graphically illustrates the total $BO_2^*$ chemiluminescent intensity and global $NO_x$ production rate as a function of Reynolds number.

In accordance with the invention, an additive for providing species to undergo an analog reaction may be homogeneously distributed in the fuel flow or the air/oxidant flow; or such seed compounds may be distributed in both flows. Introducing the seed with the fuel and/or the air in this manner defines its local concentration distribution in a diffusion flame, and impacts its thermal and chemical history prior to reaching a region of significant pollutant formation. Other possibilities include selectively introducing a seed material, for example, at a specific locus within a fuel injector, in the combustion or other reaction volume, or into a particular air or fuel stream as it enters the combustion volume. This variety in possible means of introducing the seed material(s) affords some selectivity in selecting particular regions of the combustion volume for measurement.

Measurement of the chemiluminescent intensity can be performed in any of a variety of ways, with a corresponding range of information available regarding the temporal and spatial distribution of the intensity, and correspondingly, of the pollutant formation rate distribution within the reaction volume. For example, photographic imaging, although it does not directly resolve values along the optical axis, can provide a two dimensional map of the total intensity integrated along each optical line of sight. This integration is performed assuming that the combustion medium is essentially transparent to the emitted chemiluminescence band(s); this assumption is usually correct for gas-fired combustion systems. The images can be recorded using either conventional photographic film, digital cameras (such as charge-coupled or charge-injection devices) or a video system. Photographic film is more readily adaptable to obtaining high speed sequence images, while video can include a time-gated image intensifier, allowing a shorter exposure duration for improved resolution of moving flows and enhancing sensitivity to allow a lower concentration of seed material to be used.

Taking multiple images simultaneously along different optical paths is possible in cases wherein extensive optical access to the reaction volume is available; this aggregation of data allows tomographic reconstruction of the three-dimensional flow field.

An alternative to photographic and video techniques is an intrusive probe carrying an imaging lens and imaging fiber optic transmission bundle. This approach has the advantage of providing a relatively fine-scale spatial resolution within a reaction volume. Also, such a probe can be moved within the volume, enabling mapping of the intensity within the volume, without requiring extensive optical access to it. This feature allows operation of the method of the invention in a pressurized system and is suitable for collecting chemiluminescence data in an optically dense combustion volume, such as a high-pressure liquid-fueled combustor.

Yet another means of monitoring the chemiluminescence distribution is based on photodetectors such as photodiodes. A single such sensor could be equipped with optics to provide a narrow field of view through the combustion volume, and would deliver a time-varying intensity signal for this optical path. Obviously, multiple such paths could be used and their signals cross-correlated to establish convection time scales for large-scale flow structures. Alternatively, using two such sensors having optical paths crossing at a volume in the combustion volume would allow establishing the time-means condition at the crossing volume by signal cross-correlation.

The system of the invention is especially suitable as a tool for research into combustion and for development of combustion systems. The method outlined herein is appropriate both for broadly characterizing the distribution of a pollutant such as NO formation within a complex flow field, and to monitor detailed spatial and temporal production rate.

Another application of the invention is monitoring and improving the performance of existing combustors or burners. Typically, a burner interacts with its operating environment—for example in a multi-burner utility boiler—and requires optimization of fuel and air flow distribution in this environment to minimize pollutant formation while maintaining high overall combustion efficiency. This has commonly been done by varying flow distributions while monitoring global combustion product composition for the boiler. The chemiluminescence-based technique of the invention allows precise adjustment of each burner to minimize its production of the pollutant of interest while the other burners continue to operate. Furthermore, this procedure can be performed on a regular basis, to detect changes in the burners and boiler unit over time, for example due to burner component wear and fouling of boiler walls and flow passages.

The method of the invention is not limited to use for detecting a particular pollutant or to the study of any particular class of combustor configuration. Techniques for monitoring chemiluminescence such as are known to those of skill in the art are suitable for use in the system of the invention. The following examples illustrate observation of correlation between NO formation in combustion systems and transition of excited $BO_2^*$ to the ground state with concomitant generation of green chemiluminescence, around 540 nm.

EXAMPLES

Example 1

NO production has been monitored during hydrogen and methane combustion in a trial turbulent jet diffusion flame apparatus, of a type described in the literature (see, for example, Driscoll et al, *Combustion and Flame*, 88, 37 [1992] or Chen et al, "Nitric Oxide Levels of Jet Difflusion Flames: Effects of Coaxial Air and Other Mixing Parameters", pages 281–88, Twenty-third Symposium on Combustion, The Combustion Institute [1991]). This trial apparatus included a coaxial air nozzle (0.87 cm in diameter) within which the fuel tube was located. The trial apparatus differed from that recited in the aforementioned references in that the enclosure for the flame was square, rather than circular, in cross-section, in order to allow better viewing of emitted light. The fuel and boron seed compounds were measured and metered separately before mixing; the quantity of seed compound used in these examples were not sufficiently high to affect the global combustion process or the NO formation rate.

Chemiluminescence in the flame was observed using several techniques. In one approach, a calibrated silicon photodiode detector with a color correction filter was used to measure absolute chemiluminescence emission intensities from the flame. A short focal length microlens imaged the flame onto the detector to produce a uniform response for all regions of the flame.

In another approach, standard photographic images of the turbulent flames were acquired with a 35 mm camera using 3200 ASA color film. Exposure times as short as 0.5 millisecond were used.

Both of these configurations included an interference filter centered at 550 nm with a 40 nm FWHM bandwidth to isolate the $BO_2^*$ chemiluminescence from background light and other flame emission sources.

In yet another approach, digital images of the turbulent flames were acquired using a charge-coupled device ("CCD") imager, such as the Meade Pictor model 216XT, which has a 336×242 pixel (3.3×2.4 mm) array. A narrow band interference filter centered at 546 nm (Hg line) isolates the chemiluminescence of interest and reduces the light level for such an imager. Cooling the CCD element reduces dark current for low light level images. Minimum exposure times of 4 ms are used with this type of imager.

A 5% mixture of diborane in gaseous hydrogen (Voltaix, Inc.) served as seed compound. The seeding rate was 0.055% diborane in a stoichiometric mixture of fuel and air; for the corresponding air/fuel ratio of 2.382, the required seed concentration is 0.185% diborane in the hydrogen fuel. A 0.244 cm nozzle diameter was used. In FIG. 1, curve 10 shows the total $BO_2^*$ chemiluminescent intensity measured by the silicon photodetector as a function of Reynolds number, for the entire volume of the hydrogen jet flame. (The chemiluminescent intensity units are $10^{-8}$ W for a collection solid angle of $3\times10^{-5}$ sr, so that the highest emission intensity value of 6 corresponds to an emission intensity of $$\frac{6\times10^{-8}}{3\times10^{-5}} = 2\times10^{-3}$$

W/sr in the passband of the 550 nm interference filter.) The chemiluminescent intensity shows excellent correlation with the global $NO_x$ production rate calculated from the $NO_x$ emission index ("EINOX") reported in the aforementioned references, represented by curve 12. Spatially resolved photographic and CCD images for this family of hydrogen jet flames showed a clear increase in the chemiluminescent intensity with increasing Reynolds number, at least up to values of 9,000.

Figure 2:
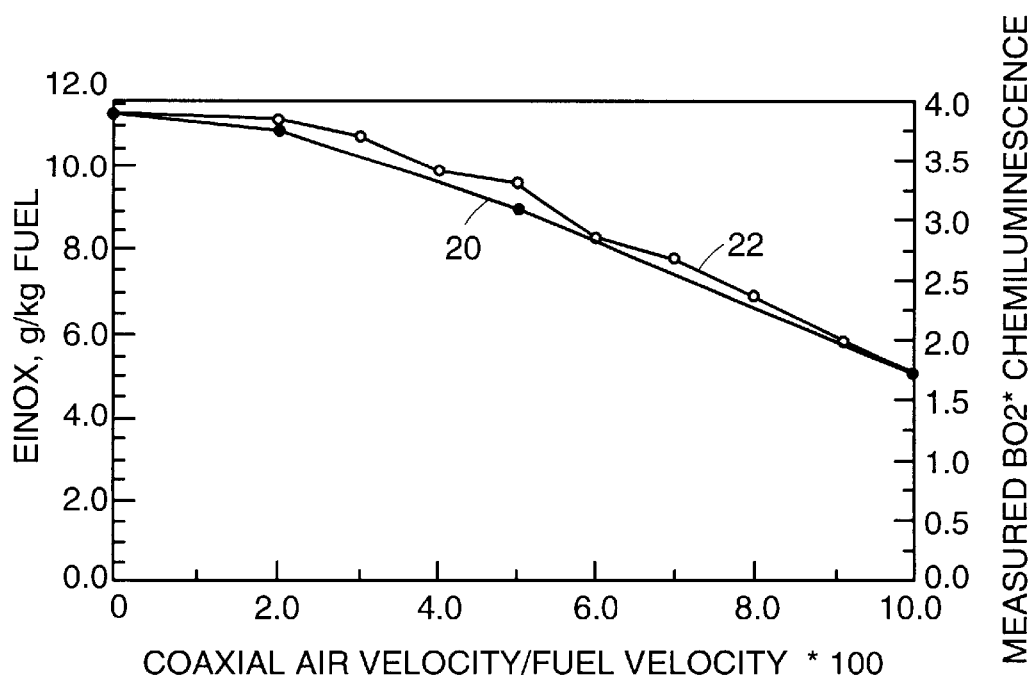
FIG. 2 graphically illustrates the total $BO_2^*$ chemiluminescent intensity and global emission index as a function of the ratio of coaxial air velocity to fuel velocity, expressed as a percentage.

In FIG. 2, curve 20 shows the total chemiluminescent intensity measured as a function of the ratio of coaxial air velocity to fuel velocity, expressed as a percentage. Adding coaxial air produces more rapid mixing of the fuel and air and increases turbulence; both of these effects shorten the flame length and decrease the $NO_x$ production rate and emission index for hydrogen flames. (Under the constant fuel flow rate conditions of the tests, the $NO_x$ production rate differs from the EINOX only by the fuel flow rate—a constant parameter.) Curve 20 shows good agreement with curve 22, representing the emission index. The same trend versus coaxial air velocity was evident in the photographic and CCD images.

In hydrogen seeded with diborane, the $BO_2^*$ chemiluminescence intensity has been found to vary linearly with a slope of approximately unity as the seeding concentration is varied by a factor of eight, from about 0.093% to 0.740% $B_2H_6$ in the fuel. This behavior indicates that by increasing the seeding rate, the approach of the invention can be adapted to detection techniques and other experimental exigencies requiring higher chemiluminescence intensities.

Example 2

For methane combustion, similar trials have been done using fuel tube diameters of 0.244 and 0.37. Diborane at 5% in nitrogen gas (Voltaix, Inc.) served as seed compound. For the desired diborane seeding rate of 0.055%, with the stoichiometric molar air to fuel ratio of 9.5, the seed concentration was 0.58% diborane in the $CH_4$ fuel. Luminescence interpretation for this fuel was complicated by soot luminescence, which had an intensity roughly five times that of the $BO_2^*$ chemiluminescence for attached flames in the bandpass region of the 550 nm interference filter; the narrower Hg line filter used with the CCD decreased this factor to four. Comparing radiation from the seeded fuel with radiation from a fuel in which the seed compound flow was replaced by pure nitrogen diluent allowed identification of the relative contributions of the chemiluminescent sources. The addition of coaxial air produces the blue, nonluminous flame that is more typical of methane flames in typical combustion devices. For instance, 5% coaxial velocity for a fuel jet Reynolds number of 2300 in the 0.244-cm diameter fuel tube results in a chemiluminescent emission almost solely due to the excited $BO_2^*$ transition. In general, for conditions under which soot formation is minimized, $BO_2^*$ chemiluminescence is the main visible emission mechanism in methane flames. Discrimination between emissions due to soot and those from the transition of interest can be enhanced by observing the $BO_2^*$ bands at 518 nm and/or 492 nm, where the soot luminescence is much weaker. Pulsing the seed injection into the fuel would also assist distinguishing the two emission sources. Increasing the seed concentration is another option.

Example 3

A premixed flat flame burner (McKenna Products) was used in conjunction with a monochrometer (Spex 0.25 meter) to observe the wavelength dependence of the macroscale $BO_2^*$ chemiluminescence emitted from hydrogen and methane flames. Slit widths on the order of 2.5 mm or 5 mm provided a low but adequate resolution spectrum of the flame emission. The silicon photodiode detector used for the radiometric measurements of jet flames described above was used as the detector for the spectral measurements. In addition to the seed compounds introduced as already specified in the foregoing examples, trimethylborate ($B(OCH_3)_3$) was also successfully used. Trimethylborate (boiling point 68° C.) was added to the fuel flow by diverting a controlled portion of the fuel flow through a bubbler, allowing it to entrain an unknown amount of trimethylborate vapor, and then recombining it with the main fuel flow.

Although the most direct technique for using the intensity of a chemiluminescent signal generated by an analog reaction to determine the formation rate of the pollutant from the intensity is to use the quantitative correlation between the pollutant production and the analog reaction to convert the signal into a rate, the invention also encompasses less direct, less quantitative routes for using the chemiluminescent signals. For example, chemiluminescence due to decay of excited $BO_2^*$ could be used to visualize the concentration of oxygen atom radicals, which could in turn be used with other data to determine NO formation patterns.

It will therefore be seen that the foregoing represents a highly advantageous approach to monitoring pollutant formation in combustion systems, especially nitrogen oxide.

The terms and expressions employed herein are used as terms of description and not of limitation, and there is no intention, in the use of such terms and expressions, of excluding any equivalents of the features shown and described or portions thereof, but it is recognized that various modifications are possible within the scope of the invention claimed.

What is claimed is:

1. A method of measuring the formation rate of a pollutant formed via a selected reaction mechanism due to a combustion reaction of reactants in a combustion system, the pollutant being formed in a reaction volume by the selected mechanism, the method comprising the steps of:
   a. observing a chemiluminescent signal generated in the reaction volume by an analog reaction instantaneously and locally correlating with the formation of the pollutant, the chemiluminescent signal having an intensity, the analog reaction analogous to a reaction step in the mechanism; and
   b. determining the formation rate of the pollutant via the selected mechanism from the intensity of the signal.

2. The method of claim 1 wherein at least one naturally occurring combustion radical undergoes the analog reaction.

3. The method of claim 2 wherein the at least one naturally occurring combustion radical is a hydroxyl radical.

4. The method of claim 1 wherein the pollutant is nitric oxide and the analog reaction correlates with the prompt mechanism of nitric oxide formation.

5. The method of claim 4 wherein excited hydroxyl radical reacts to emit the chemiluminescent signal.

6. The method of claim 1 further comprising the step of adjusting operation of the combustion system based on the monitored intensity.

7. The method of claim 1 further comprising the step of choosing features of a combustor based on the monitored intensity.

8. The method of claim 1 wherein the step of observing a chemiluminescent signal is performed using an imaging lens and imaging fiber optic transmission bundle, the imaging lens being located in the reaction volume.

9. The method of claim 1 wherein the step of observing a chemiluminescent signal is performed using at least one photodiode.

10. The method of claim 1 wherein the step of observing a chemiluminescent signal is performed using a digital camera.

11. The method of claim 1 wherein the analog reaction correlates with a rate-limiting step in the formation of the pollutant.

12. The method of claim 1 including the step of introducing a boron-containing additive into the combustion system such that combustion of the additive provides a BO radical that provides said chemiluminescent signal.

13. The method of claim 12 wherein the analog reaction correlates with the thermal mechanism of nitride oxide generation.

14. A method of measuring the formation rate of a pollutant formed due to a combustion reaction of reactants in a combustion system, the pollutant being formed in a reaction volume, the method comprising the steps of:
   a. introducing an additive into the combustion system;
   b. observing a chemiluminescent signal generated in the reaction volume by an analog reaction instantaneously and locally correlating with the formation of the pollutant, the chemiluminescent signal having an intensity, the additive providing a species that undergoes the analog reaction in the reaction volume to generate the chemiluminescent signal; and
   c. determining the formation rate of the pollutant from the intensity.

15. The method of claim 14 wherein the step of determining the formation rate of the pollutant comprises determining said rate at at least one specific time and location in the reaction volume.

16. The method of claim 14 wherein the step of determining the formation rate of the pollutant comprises determining said rate for the entire reaction volume.

17. The method of claim 14 wherein the combustion reaction occurs in a combustion volume, the combustion volume being the reaction volume.

18. The method of claim 14 wherein a post-combustion reaction occurs in a post combustion volume, the post-combustion volume being the reaction volume.

19. The method of claim 14 wherein the step of introducing an additive into the combustion system comprises injecting the additive into the combustion volume.

20. The method of claim 14 wherein a post-combustion reaction occurs in a post-combustion volume, and the step of introducing an additive into the combustion system comprising injecting the additive into the post-combustion volume.

21. The method of claim 14 wherein the pollutant is nitric oxide.

22. The method of claim 21 wherein the analog reaction correlates with the thermal mechanism of nitride oxide formation.

23. The method of claim 14 wherein the additive is a boron compound.

24. The method of claim 23 wherein BO radical is produced from the additive in the combustion system and is oxidized in the analog reaction.

25. The method of claim 14 wherein the additive is diborane.

26. The method of claim 14 wherein the additive is a trialkyl borate.

27. The method of claim 26 wherein the additive is trimethyl borate.

28. The method of claim 26 wherein the additive is triethyl borate.

29. A method of measuring the formation rate of nitric oxide formed due to a combustion reaction of reactants in a combustion system, the nitric oxide being formed in a reaction volume, the method comprising the steps of:
   a. introducing a boron compound into the combustion system, combustion of said compound providing excited $BO_2^*$;
   b. observing a chemiluminescent signal generated in the reaction volume by photon emission instantaneously and locally correlating with the formation of the nitric oxide, the chemiluminescent signal having an intensity; and
   c. determining the formation rate of the nitric oxide from the intensity.

* * * * *